(12) United States Patent
Maidens et al.

(10) Patent No.: US 12,303,237 B2
(45) Date of Patent: May 20, 2025

(54) METHODS AND SYSTEMS FOR PULMONARY ARTERY PRESSURE AND CARDIAC SYNCHRONIZATION MONITORING

(71) Applicant: Eko Health, Inc., Emeryville, CA (US)

(72) Inventors: John Maidens, Berkeley, CA (US); Ling Guo, San Francisco, CA (US); Subramaniam Venkatraman, Lafayette, CA (US); Connor Landgraf, Martinez, CA (US)

(73) Assignee: EKO HEALTH, INC., Emeryville, CA (US)

( * ) Notice: Subject to any disclaimer, the term of this patent is extended or adjusted under 35 U.S.C. 154(b) by 227 days.

(21) Appl. No.: 17/453,281

(22) Filed: Nov. 2, 2021

(65) Prior Publication Data
US 2023/0134653 A1    May 4, 2023

(51) Int. Cl.
*A61B 5/0205*    (2006.01)
*A61B 5/00*    (2006.01)
(Continued)

(52) U.S. Cl.
CPC ........ *A61B 5/0205* (2013.01); *A61B 5/02028* (2013.01); *A61B 5/02108* (2013.01);
(Continued)

(58) Field of Classification Search
CPC .............. A61B 5/0205; A61B 5/02028; A61B 5/02108; A61B 5/0816; A61B 5/1102;
(Continued)

(56) References Cited

U.S. PATENT DOCUMENTS 9,736,625 B1    8/2017    Landgraf et al.
D810,944 S    2/2018    Goolkasian
(Continued)

FOREIGN PATENT DOCUMENTS

EP    3760107 A1 *    1/2021    ........... A61B 5/0006
WO    WO-2019152699 A1 *    8/2019
(Continued)

OTHER PUBLICATIONS https://www.mayoclinic.org/diseases-conditions/cardiomyopathy/symptoms-causes/syc-20370709 (Year: 2023).*
(Continued)

*Primary Examiner* — Shirley X Jian
*Assistant Examiner* — Laura Hodge
(74) *Attorney, Agent, or Firm* — McCoy Russell LLP

(57) ABSTRACT

Various methods and systems are provided for monitoring a pulmonary artery pressure and cardiac synchronization of a subject. In one example, a method includes acquiring at least one of electrocardiogram (ECG) data, phonocardiogram (PCG) data, and seismocardiogram (SCG) data from a subject via a digital stethoscope, inputting one or more of the ECG data, the PCG data, and the SCG data into a machine learning algorithm, and estimating at least one of a pulmonary artery pressure and a cardiac synchronization of the subject using the machine learning algorithm. In this way, the pulmonary artery pressure and the cardiac synchronization may be estimated using artificial intelligence and inputs that are non-invasively measured by the digital stethoscope, allowing conditions like heart failure and pulmonary hypertension to be more simply and reliably detected and monitored.

15 Claims, 5 Drawing Sheets

(51) Int. Cl.

| | | |
|---|---|---|
| *A61B 5/02* | (2006.01) | |
| *A61B 5/021* | (2006.01) | |
| *A61B 5/08* | (2006.01) | |
| *A61B 5/11* | (2006.01) | |
| *A61B 5/1455* | (2006.01) | |
| *A61B 5/318* | (2021.01) | |
| *A61B 5/33* | (2021.01) | |
| *A61B 7/04* | (2006.01) | |

(52) U.S. Cl.
CPC .......... *A61B 5/0816* (2013.01); *A61B 5/1102* (2013.01); *A61B 5/14551* (2013.01); *A61B 5/318* (2021.01); *A61B 5/33* (2021.01); *A61B 5/4842* (2013.01); *A61B 5/7264* (2013.01); *A61B 5/7275* (2013.01); *A61B 5/7475* (2013.01); *A61B 7/04* (2013.01); *A61B 2562/0219* (2013.01)

(58) Field of Classification Search
CPC ....... A61B 5/33; A61B 5/7264; A61B 5/7275; A61B 7/04
See application file for complete search history.

(56) References Cited

U.S. PATENT DOCUMENTS

| | | | |
|---|---|---|---|
| 9,973,847 B2 | 5/2018 | Wong | |
| D851,253 S | 6/2019 | Goolkasian | |
| 10,945,624 B2 | 3/2021 | Landgraf et al. | |
| D941,468 S | 1/2022 | Freschl et al. | |
| 2007/0273504 A1 | 11/2007 | Tran | |
| 2008/0013747 A1 | 1/2008 | Tran | |
| 2010/0222723 A1* | 9/2010 | Hoffmann | A61N 7/00 601/107 |
| 2015/0038856 A1* | 2/2015 | Houlton | A61B 5/6826 600/484 |
| 2016/0100817 A1* | 4/2016 | Hussain | A61B 7/04 600/528 |
| 2018/0116626 A1* | 5/2018 | Darbari | A61B 5/02055 |
| 2018/0228468 A1* | 8/2018 | Adler | A61B 8/5223 |
| 2018/0317789 A1* | 11/2018 | Ransbury | A61B 5/308 |
| 2019/0000413 A1* | 1/2019 | Adler | H04R 1/406 |
| 2020/0107745 A1 | 4/2020 | Landgraf et al. | |
| 2020/0242566 A1* | 7/2020 | Agarwal | G06N 7/01 |
| 2021/0153776 A1* | 5/2021 | Minar | A61B 5/1076 |
| 2021/0153837 A1* | 5/2021 | Jones | A61B 5/0205 |
| 2021/0161452 A1 | 6/2021 | Landgraf et al. | |
| 2021/0259560 A1 | 8/2021 | Venkatraman et al. | |
| 2021/0345934 A1 | 11/2021 | Landgraf et al. | |
| 2021/0345939 A1* | 11/2021 | Jumbe | H04R 1/028 |
| 2022/0095955 A1* | 3/2022 | Shadforth | A61B 5/0002 |

FOREIGN PATENT DOCUMENTS

| | | | |
|---|---|---|---|
| WO | 2020041363 A1 | 2/2020 | |
| WO | WO-2021229512 A1 * | 11/2021 | .......... A61B 5/1113 |
| WO | 2021245203 A1 | 12/2021 | |
| WO | 2022064464 A1 | 3/2022 | |
| WO | 2022211972 A1 | 10/2022 | |

OTHER PUBLICATIONS https://www.mayoclinic.org/diseases-conditions/heart-valve-disease/symptoms-causes/syc-20353727 (Year: 2023).*
https://www.mayoclinic.org/diseases-conditions/myocardial-ischemia/symptoms-causes/syc-20375417 (Year: 2023).*
Great Britain Intellectual Property Office, Search Report under Section 17(5) Issued in Application No. GB2215427.2, Apr. 3, 2023, 4 pages.
Venkatraman, S. et al., "Methods and Systems for Remote Health Monitoring, " U.S. Appl. No. 16/997,464, filed Aug. 19, 2020, 83 pages.
Donovan, N. et al., "Electronic Stethoscope Device With Noise Cancellation," U.S. Appl. No. 17/274,071, filed Mar. 5, 2021, 48 pages.
Venkatraman, S. et al., "Systems and Methods for Electronic Stethoscope Wireless Auscultation, " U.S. Appl. No. 17/313,842, filed May 6, 2021, 69 pages.
Blair, R. et al., "Methods and Systems for Automated Clinical Workflows," U.S. Appl. No. 17/449,436, filed Sep. 29, 2021, 65 pages.

* cited by examiner

METHODS AND SYSTEMS FOR PULMONARY ARTERY PRESSURE AND CARDIAC SYNCHRONIZATION MONITORING

FIELD

The present description relates generally to medical devices utilizing non-invasive monitoring.

BACKGROUND/SUMMARY

Heart failure is a leading cause of morbidity and mortality. It is the most common cause of hospitalization and is a significant economic burden. Early detection and initiation of treatment, as well as careful monitoring and adjustment of treatment, are desired to reduce disease burden.

Pulmonary hypertension is a syndrome that describes increased pressure in the pulmonary circulation and is defined as having mean pulmonary artery pressure greater than 20 mmHg at rest, as measured by invasive right heart catheterization. Pulmonary hypertension is a common comorbidity of heart failure but can also have other causes. Regardless of the cause, pulmonary hypertension has a poor prognosis without early intervention and is associated with increased hospitalizations and mortality.

Diagnosis of heart failure and pulmonary hypertension is challenging because physical symptoms, such as dyspnea, are often non-specific. Patients presenting with such symptoms are first evaluated by emergency or general practitioners who have poorer diagnostic accuracy than trained cardiologists. A referral for echocardiography is also used for further evaluation. Echocardiography is a non-invasive tool for assessing heart failure and pulmonary hypertension but does not detect all types of heart failure (e.g., heart failure with preserved ejection fraction) and does not confirm pulmonary hypertension (which uses invasive heart catheterization). It is also expensive, and successful diagnosis can be operator-dependent. Hence, a rapid and non-invasive screening tool for heart failure and pulmonary hypertension at a point-of-care setting, usable by minimally trained personnel, is an unmet clinical need for the early identification and intervention of patients at risk.

In one example, the issues described above may be addressed by a method, comprising: acquiring at least one of electrocardiogram (ECG) data, phonocardiogram (PCG) data, and seismocardiogram (SCG) data from a subject via a digital stethoscope, inputting one or more of the ECG data, the PCG data, and the SCG data into a machine learning algorithm, and estimating at least one of a pulmonary artery pressure and a cardiac synchronization of the subject using the machine learning algorithm. In this way, the pulmonary artery pressure and cardiac synchrony may be estimated using artificial intelligence and inputs that are non-invasively measured by the digital stethoscope, allowing heart failure and pulmonary hypertension to be more simply and reliably detected and monitored. As a result, positive patient outcomes may be increased with a decreased burden on the healthcare system and the patient.

It should be understood that the brief description above is provided to introduce in simplified form a selection of concepts that are further described in the detailed description. It is not meant to identify key or essential features of the claimed subject matter, the scope of which is defined uniquely by the claims that follow the detailed description. Furthermore, the claimed subject matter is not limited to implementations that solve any disadvantages noted above or in any part of this disclosure.

BRIEF DESCRIPTION OF THE DRAWINGS

The present disclosure will be better understood from reading the following description of non-limiting embodiments, with reference to the attached drawings, wherein below.

DETAILED DESCRIPTION

Figure 1A:
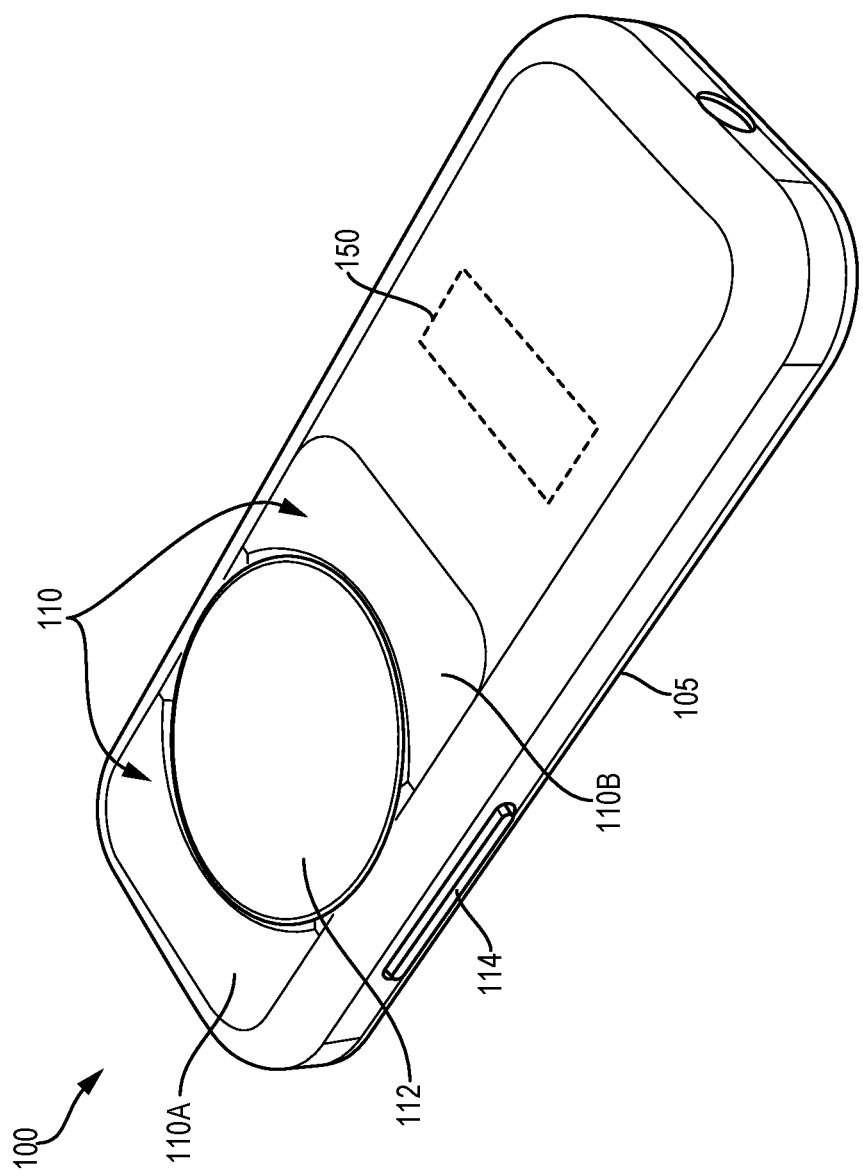
FIG. 1A shows a front perspective view of an exemplary electronic stethoscope.
Figure 1B:
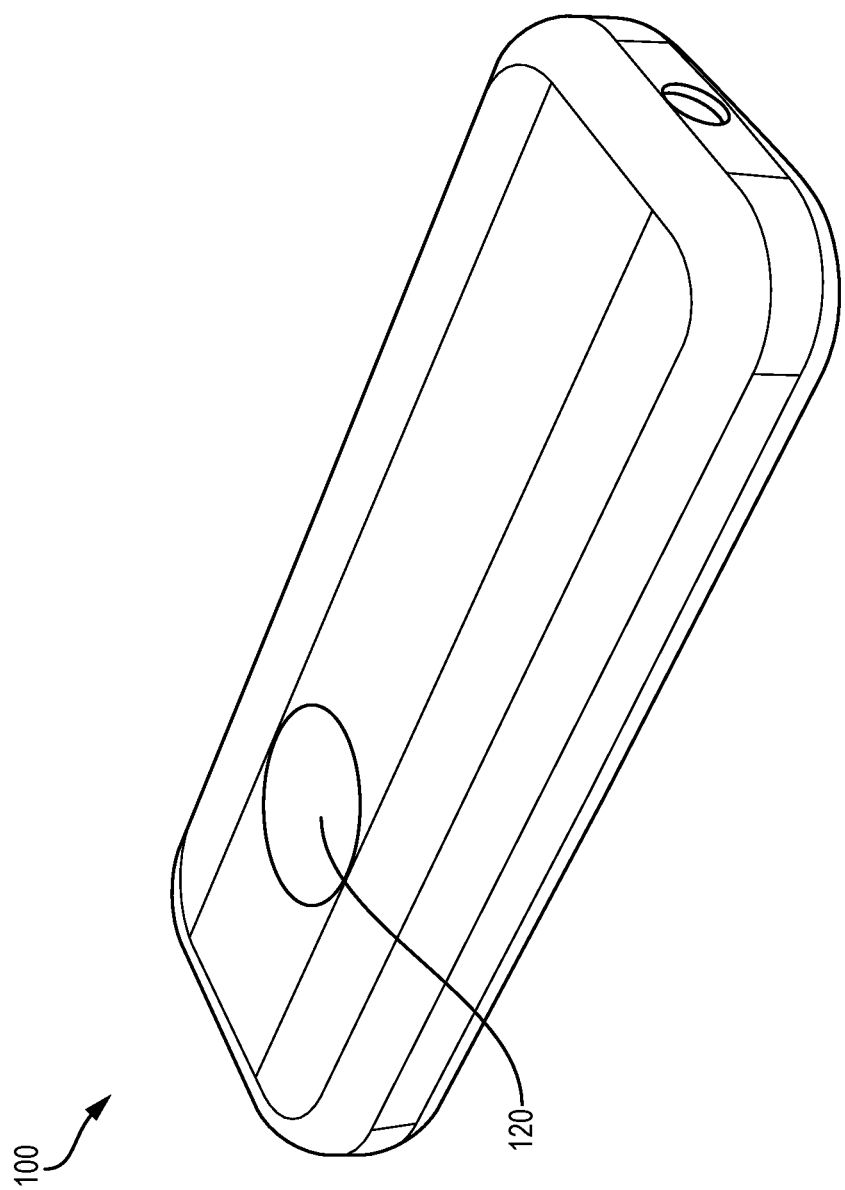
FIG. 1B shows a back perspective view of the exemplary monitoring device of FIG. 1A.
Figure 2:
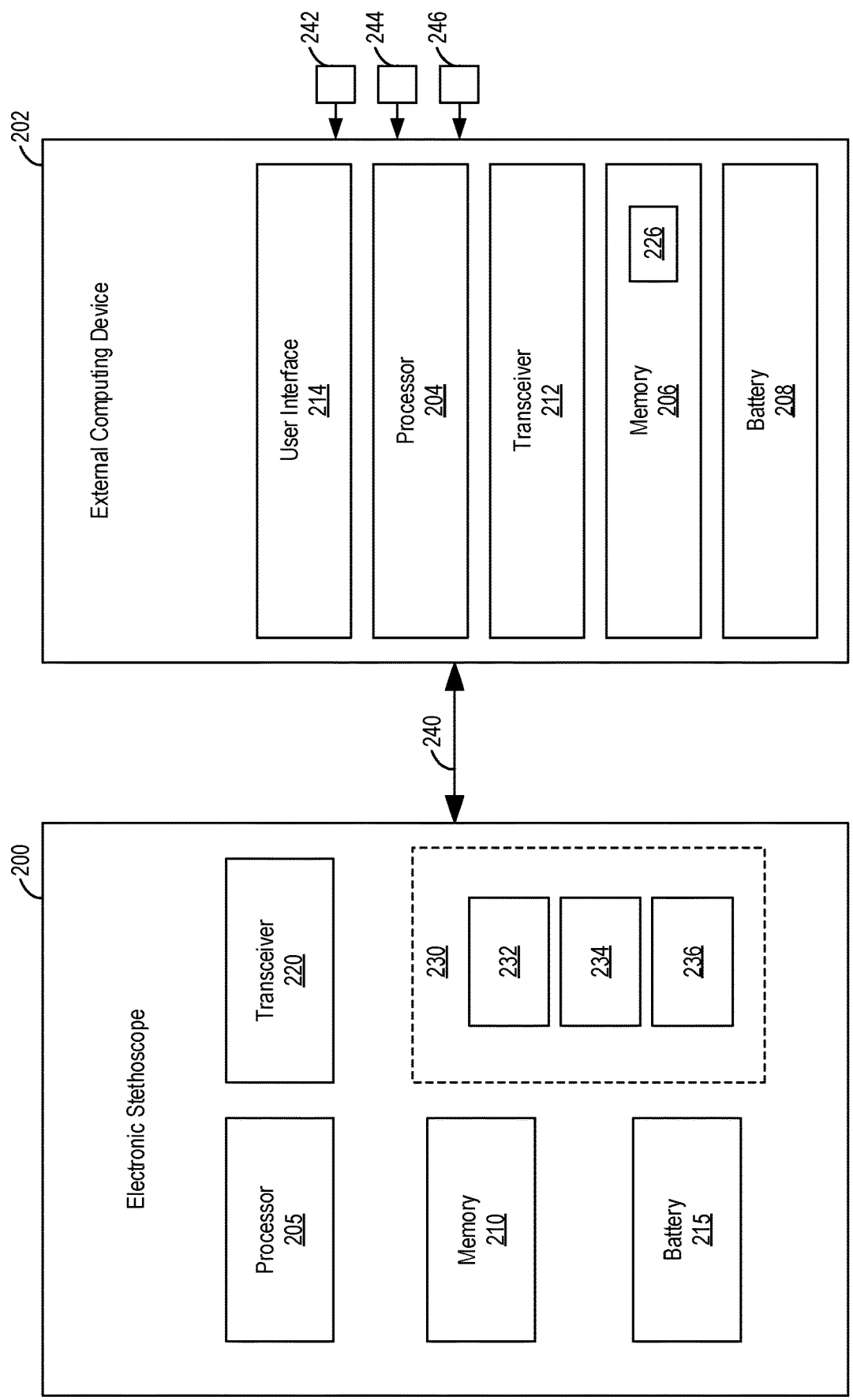
FIG. 2 shows a schematic of an interior of an electric stethoscope and an interior of an external computing device, both in communication with each other.

The following description relates to systems and methods for digital health monitoring, such as using the electronic stethoscope shown in FIGS. 1A and 1B, also referred to herein as a digital stethoscope. In some examples, the electronic stethoscope may be in communication with an external computing device, such as shown in FIG. 2, in order to transmit recorded physiological data for processing at the external computing device. The physiological data may include electrocardiogram (ECG) data, seismocardiogram (SCG) data, and/or phonocardiogram (PCG) data, for example, and may be utilized by a machine learning algorithm to determine pulmonary artery pressure and cardiac synchronization, such as according to the method of FIG. 3. The pulmonary artery pressure and the cardiac synchronization may be further utilized to identify and/or monitor heart failure and pulmonary hypertension, such as illustrated in the block diagram of FIG. 4.

Turning now to the figures, FIG. 1A shows a top view of an electronic stethoscope 100 comprising a housing 105, which encases sensors and control circuitry. The electronic stethoscope 100 may also be referred to herein as a digital stethoscope. The shape and design of the housing 105 may facilitate a subject's comfort during monitoring a state or condition of the subject. Additionally, the shape and design of the housing 105 may facilitate a secure fit against a variety of patient body types and shapes in order to increase sensor contact and with adequate sensor geometry.

The electronic stethoscope 100 may comprise one or more sensors. In some examples, the electronic stethoscope 100 comprises at least three sensors (e.g., sensor modalities). The sensors may be various types of sensors, such as ECG sensors, audio sensors, temperature sensors, pressure sensors, vibration sensors, force sensors, respiratory monitors or sensors (e.g., a device, device part, or sensor capable of measuring a respiration rate), heart rate monitors or sensors, intrathoracic impedance monitors or sensors (e.g., a device, device part, or sensor capable of measuring an intrathoracic impedance), accelerometers, and/or other types of sensors. The sensors may be part of the electronic stethoscope 100.

In other examples, the sensors may be coupled with or otherwise configured to be used in combination with the electronic stethoscope 100.

The electronic stethoscope 100 comprises an electrical sensor 110 of a first sensor modality and an audio sensor 112 of a second sensor modality positioned on an exterior of the housing 105. In the illustrated example, the electrical sensor 110 includes a first electrode 110A and a second electrode 110B, however, other numbers of electrodes are possible. For example, the electrical sensor 110 may include 4 electrodes. For example, the first electrode 110A and the second electrode 110B may be ECG transducer electrodes, which may measure electrical signals from a patient resulting from depolarization of the heart muscle during a heartbeat. In the illustrated example, the first electrode 110A and the second electrode 110B include contact pads for obtaining ECG data, and thus, the electrical sensor 110 may be an ECG sensor.

Additionally or alternatively, the first electrode 110A and the second electrode 110B may comprise a current injection electrode and a voltage measurement electrode, respectively, for intrathoracic impedance measurements. For example, each of the first electrode 110A and the second electrode 110B may be used to measure both electrocardiogram (ECG) data and intrathoracic impedance data. Measuring intrathoracic impedance may provide information about a presence or the amount of a fluid in the lungs of the subject. For example, intrathoracic impedance may decrease as an amount of a fluid in the lung or lungs increases. The reason for this may be that the fluid may conduct electrical current. Data collected using intrathoracic impedance sensors may provide insight and information about the condition of the lungs of the subject and identify potential signs of decompensation, pulmonary edema, or any state or condition of the subject correlated with the presence of fluid in lungs. For example, wheezes, crackles and rhonchi are often heard in lung sounds due to fluid accumulation in the lungs. Therefore, the intrathoracic impedance measurement may be used in conjunction with lung sounds obtained by the audio sensor 112 to provide a joint measure of fluid retention.

The audio sensor 112 may comprise a surface for obtaining audio data. The audio sensor 112 may include one or more microphones units for collecting audio data, also referred to herein as phonocardiogram (PCG) data. The audio sensor 112 may capture longitudinal waves (e.g., oscillations) of chest wall of the subject emanating from the heart. For example, the audio sensor 112 may capture higher frequency (e.g., greater than 20 Hz) oscillations.

It may be understood that additional sensor modalities may be positioned internal to the housing 105, such as an accelerometer 150. The accelerometer 150 may comprise a three-axis accelerometer, which may provide information about the orientation and motion of the electronic stethoscope 100. The accelerometer 150 may be rigidly affixed to a surface within the electronic stethoscope 100 so that the accelerometer 150 does not move independently from the electronic stethoscope 100 as a whole. Further, the accelerometer 150 may be used to record seismocardiogram (SCG) data corresponding to lower frequency oscillations (e.g., less than 50 Hz) of the chest wall of the subject. Further, the accelerometer 150 may capture both longitudinal and transverse oscillations. Thus, the audio sensor 112 may capture higher frequency longitudinal chest oscillations emanating from the heart, whereas the accelerometer 150 may capture lower frequency longitudinal and transverse chest oscillations emanating from the heart.

The electronic stethoscope 100 may additionally comprise user controls such as a button 114. The button 114 may control the intensity of a monitored signal to be transmitted to a user. The button 114 may comprise a positive end and a negative end, such that when the positive end (e.g., a first end) of the button is depressed, a signal amplitude is increased, and when a negative end (e.g., a second end opposite the first end) of the button is depressed, the signal amplitude is decreased. The signal amplitude may comprise a volume of an amplified audio signal. The audio signal may be transmitted wirelessly to an earpiece of a user (such as a healthcare provider) or do another connected electronic device.

FIG. 1B shows a bottom view of the electronic stethoscope 100. The electronic stethoscope 100 may comprise additional user controls such as a button 120. In some examples, the button 120 may be used to stop and start measurement of data by the electronic stethoscope 100. The button 120 may be actuated by a user. It may be possible to stop or start measurement without actuating the button 120, such as by controlling collection through a computing device, as will be elaborated herein with particular reference to FIG. 2.

The electronic stethoscope 100 may be used to collect ECG data, PCG data, SCG data, intrathoracic impedance data, and/or orientation data from a plurality of different locations or parts of a body of the subject, such as positions at and/or around a heart, lung, vein, or artery of the subject. In some examples, the electronic stethoscope 100 may further comprise more sensors, such as the sensors listed anywhere herein, which may be used to collect data from various parts of the subject's body. Data collection may be performed by placing the electronic stethoscope 100 or the one or more sensors at different positions adjacent to the body of the subject (e.g., in contact with the body, inside the body, or remote from the body) and using the electronic stethoscope 100 to take one or more measurements (e.g., collect ECG data, PCG data, SCG data, intrathoracic impedance data, orientation and motion data, or any other type of data) at each of at least a subset of the different positions at suitable time points and/or intervals for suitable durations of time.

The electronic stethoscope 100 may be mobile. For example, the electronic stethoscope 100 may be movable from one point to another. The electronic stethoscope 100 may be configured to be placed on and removed from the body of the subject. For example, the electronic stethoscope 100 may be placed on the body of the subject at a location in proximity to a heart, lung, or bowel of the subject. The electronic stethoscope 100 may not be implantable in the body of the subject. The electronic stethoscope 100 may be sufficiently light that it is easily transported from one location to another. For example, the electronic stethoscope 100 may weigh between 0.5 pounds and 10 pounds. As another example, the electronic stethoscope 100 may weigh less than 0.5 pounds.

The electronic stethoscope 100 may be sufficiently sized such that it may be easily transported from one location to another. The electronic stethoscope 100 may be handheld, and as such, may be sized to fit in a hand. For example, the electronic stethoscope 100 may comprise an external dimension between about 0.25 inches and about 12 inches. In another example, the external dimension may be less than 0.25 inches.

Turning now to FIG. 2, a schematic of an interior of an electronic stethoscope 200 and an interior of an external computing device 202 in communication with the electronic stethoscope 200 is shown. For example, the electronic stethoscope 200 may be the electronic stethoscope 100 shown in FIGS. 1A and 1B, or may be a similar monitoring device capable of recording various physiological data and communicating with other electronic devices, such as the external computing device 202. As another example, the external computing device 202 may be a desktop computer, a laptop computer, a cellular phone, a tablet, or another device that includes a display and is capable of communicating with other electric devices.

The electronic stethoscope 200 may comprise electrical components configured to control the operation of the various sensors. For example, the electronic stethoscope 200 may comprise devices to store data (e.g., a hard drive or memory), to transmit data, to convert analog data to digital data, to provide information on the functionality of the monitoring device, to control various aspects of data collection, etc. The electronic stethoscope 200 may comprise a microprocessor or microprocessing unit (MPU) 205, also referred to as a processor 205. The processor 205 may be operably connected to a memory 210. The processor 205 may execute a sequence of machine-readable instructions, which can be embodied in a program or software. The instructions may be directed to the processor 205, which can subsequently implement the methods or portions of the methods of the present disclosure. The machine-readable (e.g., executable) instructions may be stored in the memory 210, for example, which may be a read-only or non-transitory memory. Power may be supplied to the various components (the sensors, the microprocessors, the memory, etc.) by a battery 215. The battery 215 may be coupled to charging circuitry, which may be wireless charging circuitry.

The electronic stethoscope 200 may transmit data to the external computing device 202 (e.g., a computing device that is external to the electronic stethoscope 200), another computing device, and/or to a network (e.g., to the Cloud). The electronic stethoscope 200 may comprise a transceiver 220, such as a wireless transceiver, to transmit data to the computing device. The electronic stethoscope 200 may be connected to the Internet and/or a cellular data network. The transceiver 220 may comprise a Bluetooth transceiver, a Wi-Fi radio, etc. Various wireless communication protocols may be utilized to convey data, including Wi-Fi™, Bluetooth™, or a near-field communication (NFC) protocol.

The electronic stethoscope 200 may store data (e.g., ECG data, PCG data, SCG data, and/or data from any combination of the one or more sensors and/or any of the sensor modalities) locally on the electronic stethoscope 200. In an example, the data may be stored locally on the memory 210 (e.g., read-only memory, random-access memory, flash memory) or a hard disk. "Storage" type media can include any or all of the tangible memory of the computers, processors or the like, or associated modules thereof, such as various semiconductor memories, tape drives, disk drives and the like, which may provide non-transitory storage at any time for the software programming.

The electronic stethoscope 200 includes a sensor unit 230. The sensor unit 230 may comprise an ECG transducer package 234 including an electrical sensor (e.g., the electrical sensor 110 shown in FIG. 1A) and an analog-to-digital converter (ADC) to digitize ECG signals detected by the ECG electrodes. The ECG data may comprise single-lead ECG data. Single-lead ECG data may be obtained from one electrode that may be a ground and another electrode that may be a signal electrode. A voltage difference between the leads may comprise analog ECG signal data. ECG data can be recorded as voltage as a function of time. Alternatively, the ECG data may comprise three-lead ECG data. In still other examples, the EGC data may be obtained via more than three leads (e.g., five-lead ECG data). For example, the ECG electrodes may have between 1 and 12 leads, each capturing different vectors of the electrical polarization of the heart. As such, the ECG electrodes may capture between 1 to 12 different vectors of the electrical polarization of the heart, depending on the number of leads.

In some examples, the ECG data may comprise chest cavity, lung, and/or intrathoracic impedance measurement data. The electrical data may comprise ECG data measured from a heart, lung, or other organ of a subject. The electrical data may comprise impedance data measured from a lung or intra-thorax of a subject (e.g., intrathoracic impedance data). The electrical data may comprise ECG data measured from a bowel or other organ of a subject.

The sensor unit 230 additionally includes an audio transducer package 232 and an accelerometer 236, which may be similar or the same as the accelerometer 150 shown in FIG. 1A. The audio transducer package 232 may include an analog-to-digital converter to digitize audio signals detected by the audio sensor. The audio transducer package 232 may be used to record physiological sounds from the heart, lungs, stomach, etc. of a patient during an auscultation examination.

The electronic stethoscope 200 may be in communication with the external computing device 202 through a communication link 240. The communication link 240 may be a Bluetooth connection, internet connection, radio connection, or another type of connection that allows data to transfer between the electronic stethoscope 200 and the external computing device 202. For example, the electronic stethoscope 200 may record physiological sounds using the audio transducer package 232, and then the transceiver 220 may send the physiological data to the external computing device 202 through the communication link 240. The external computing device 202 may then receive the data by a transceiver 212. The transceiver 212 may comprise a Bluetooth transceiver, a Wi-Fi radio, etc.

The external computing device 202 may also include, but is not limited to, a user interface 214, a processor 204, a memory 206 (e.g., read-only memory, random-access memory, flash memory), and a battery 208. The battery 208 may supply power to the various components (the user interface 214, the memory 206, etc.). The battery 208 may be coupled to wireless charging circuitry, or may be charged using a charging wire. The processor 204 may comprise a microprocessor or MPU. The processor 204 may be operably connected to the memory 206. The processor 204 can execute a sequence of machine-readable instructions, which can be embodied in a program or software. The instructions can be directed to the processor 204, which can subsequently implement methods or components of methods of the present disclosure, such as a method to estimate pulmonary artery pressure and cardiac synchrony and a heart failure/pulmonary hypertension status therefrom, as will be described with reference to FIG. 3. For example, the memory 206 may include a machine learning model (or algorithm) 226 stored therein, or the machine learning model may be accessed via a network (e.g., via the Cloud). The machine learning model 226 may receive data transmitted to the external computing device 202 from the electronic stethoscope 200 (e.g., via the communication link 240), process the received data, and output the estimated pulmonary artery pressure and cardiac synchrony, such as will be elaborated with respect to FIG. 4.

The user interface 214 may include a display that shows data collected by and transmitted from the electronic stethoscope 200. For example, the display may show a shape of an ECG waveform to the user. As another example the display may show the outputs of the machine learning model 226 as well as additional parameters determined using decision logic stored within the memory 206 or otherwise accessed via the processor 204. For example, the display may show the estimated pulmonary artery pressure, the cardiac synchrony, a pulmonary hypertension status, and a heart failure status. Additionally, the user interface 214 may include input devices that enable the user to interact with the external computing device 202, such as through a touchscreen or other methods. For example, the user may control a recording status of the electronic stethoscope 200 in real-time via the user interface 214 of the external computing device 202. As used herein, the term "real-time" refers to a process executed without intentional delay. For example, "real-time" may refer to a response time of less than or equal to about 1 second, a tenth of a second, a hundredth of a second, a millisecond, or less. In some examples, "real-time" may refer to simultaneous or substantially simultaneous data generation, processing, and transmission.

The external computing device 202 may also receive data from other monitors and sensors in addition to the electronic stethoscope, represented schematically in FIG. 2 as a first sensor 242, a second sensor 244, and a third sensor 246. Although three sensors are shown, the external computing device 202 may receive information from more or fewer than three sensors in addition to the electronic stethoscope 200. The first sensor 242 may be a weight scale, the second sensor 244 may be a pulse oximeter, and the third sensor 246 may be a blood pressure monitor. One of the first sensor 242, the second sensor 244, and the third sensor 246 may additionally or alternatively include an activity monitor and a respiration monitor. As still another example, the external computing device 202 may receive patient demographic information and/or a medical history of the patient, which may be input via the user interface 214, accessed via the transceiver 212 in communication with a remote server, and/or stored in the memory 206.

Figure 3:
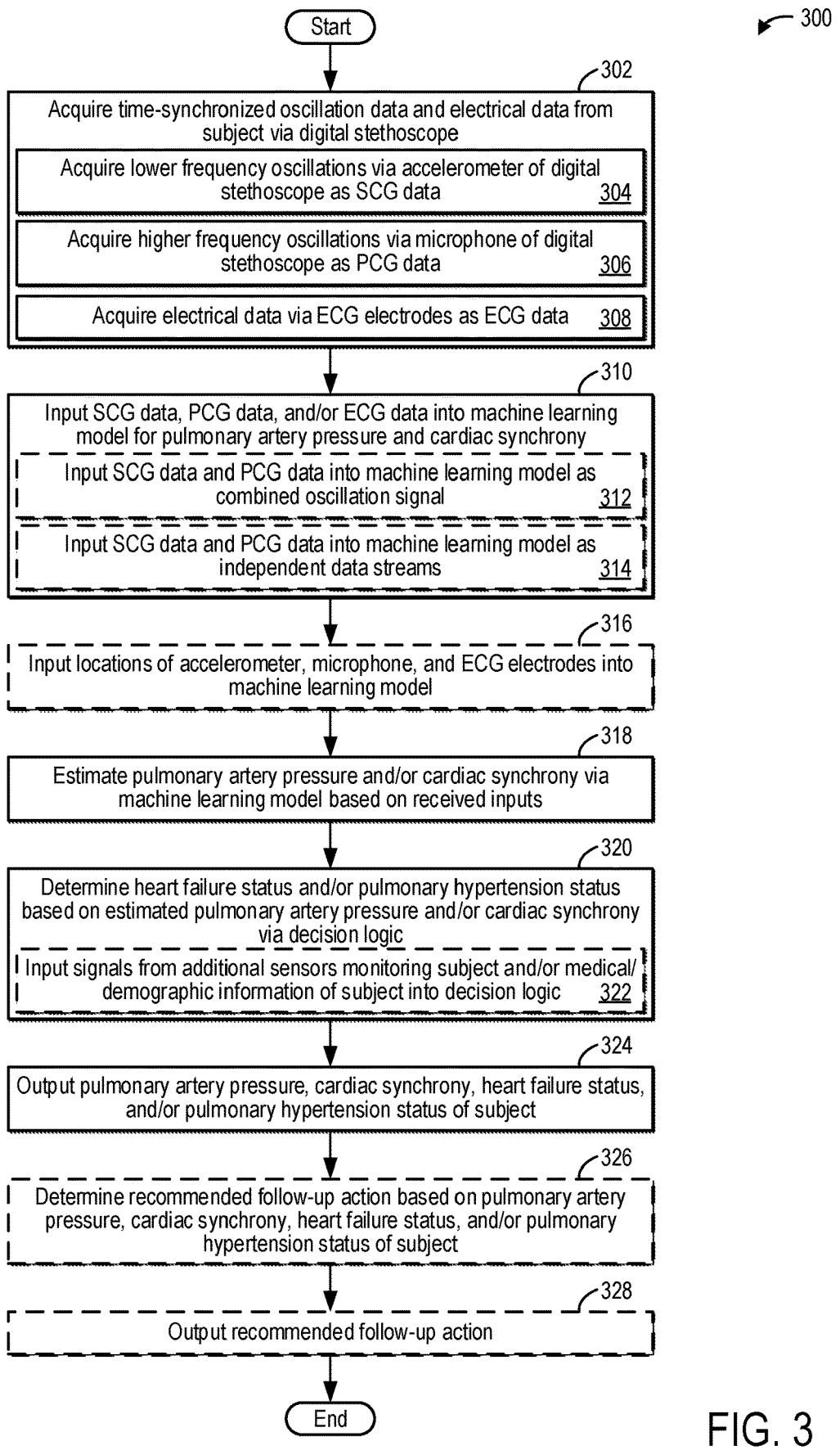
FIG. 3 shows a flowchart of a method for estimating and monitoring pulmonary artery pressure and cardiac synchronization based on signals output from an electronic stethoscope.

Turning now to FIG. 3, an example method 300 for estimating and monitoring pulmonary artery pressure and cardiac synchronization, and thus a heart failure status and a pulmonary hypertension status, based on signals output from a digital stethoscope is shown. For example, the digital stethoscope may be the electronic stethoscope 100 shown in FIGS. 1A-1B. At least a portion of the method 300 may be executed on a computing device that is external to the digital stethoscope, such as the external computing device 202 shown in FIG. 2. The method 300 may be executed by one or more processors during a cardiac exam, including a processor of the computing device (e.g., the processor 204 of FIG. 2), based on instructions stored on a memory operatively coupled to each of the one or more processors (e.g., the memory 206 of FIG. 2) and in conjunction with signals received from electronic components of the digital stethoscope. The computing device may be a desktop or laptop computer, a cellular phone, a tablet, or other computing device capable of connecting to other electronic devices, including the digital stethoscope. Furthermore, the method 300 may be executed as part of a software application stored within the computing device that enables a user to interface with the digital stethoscope wirelessly from the computing device.

At 302, the method 300 includes acquiring time-synchronized oscillation data and electrical data from a subject via the digital stethoscope. The time-synchronized oscillation data and electrical data provide views on the mechanical and electrical activation of the heart of the subject. To acquire these data, the computing device may connect to the digital stethoscope through a wireless connection, such as Bluetooth™, Wi-Fi™, radio, etc. Alternatively, the computing device may connect to the digital stethoscope via a wired connection, such as Ethernet, universal serial bus (USB), etc. The connection may place the computing device and the digital stethoscope in electronic communication with each other. For example, the digital stethoscope may transmit data to the computing device. As another example, the computing device may transmit commands to the digital stethoscope, such as a command to begin data acquisition. Additionally, the computing device may be a first computing device that is connected to a second computing device, which may be remote from the first computing device. As one example, the second computing device may be included in a Cloud computing network.

During the cardiac exam, the digital stethoscope may be positioned at a desired recording location on the subject by the user. The user may be a clinician or may be the subject. In some examples, the computing device may provide placement instructions or other instructions for the cardiac exam, such as via a user interface.

Acquiring the time-synchronized oscillation data and electrical data from the subject via the digital stethoscope includes acquiring lower frequency oscillations via an accelerometer of the digital stethoscope as SCG data, as indicated at 304. The accelerometer comprises a three-axis accelerometer, such as the accelerometer 150 introduced with respect to FIG. 1A. As mentioned above, the lower frequency oscillations may comprise longitudinal and transverse oscillations that are less than 50 Hz. For example, the oscillations may correspond to movements of the chest wall of the subject emanating from the heart, such as observed in S3 and S4 heart sounds and split S2 heart sounds.

Acquiring the time-synchronized oscillation data and electrical data from the subject via the digital stethoscope further includes acquiring higher frequency oscillations via a microphone of the digital stethoscope as PCG data, as indicated at 306. For example, the microphone may be the audio sensor 112 introduced with respect to FIG. 1A. The higher frequency oscillations may comprise longitudinal oscillations emanating from the heart that are greater than 20 Hz. Thus, longitudinal oscillations within a range from approximately 20 Hz and 50 Hz may be captured by both the accelerometer and the microphone. By capturing both the lower frequency SCG data and the higher frequency PCG data, heart oscillations across a range of frequencies from 1 Hz to greater than 2 kHz may be obtained. As a result, a likelihood that oscillations from cardiac pathologies are captured is increased.

Acquiring the time-synchronized oscillation data and electrical data from the subject via the digital stethoscope includes acquiring electrical data via ECG electrodes of the digital stethoscope as ECG data, as indicated at 308. For example, the ECG electrodes may be included in an electrical sensor of the digital stethoscope, such as the electrical sensor 110 introduced with respect to FIG. 1A. The ECG data captures electrical activity from approximately 0 Hz to 250 Hz, which measures the electrical activation of the heart. Further, the ECG data may be single-lead ECG data or three-lead ECG data, at least in some examples. In other examples, the ECG data may be captured by more than three leads, such as 12-lead ECG data. Each lead provides different vectors of electrical polarization of the heart.

At 310, the method 300 includes inputting the SCG data, the PCG data, and/or the ECG data into a machine learning model for pulmonary artery pressure and cardiac synchrony.

Pulmonary artery pressure is typically measured via invasive right heart catheterization and may be used to identify pulmonary hypertension, which is a syndrome defined as having a mean pulmonary artery pressure of at least 20 mmHg at rest. Cardiac synchrony (or synchronization) is typically determined via non-invasive but expensive echocardiographic imaging and examination by a skilled cardiologist and relates an electrical wave of the heart of a mechanical wave of the heart. For example, cardiac electrical and mechanical dyssynchrony may be a symptom of heart failure. As such, providing a machine learning model for pulmonary artery pressure and cardiac synchrony that uses non-invasively measured SCG data, PCG data, and ECG data from a handheld digital stethoscope may provide a quick, inexpensive, and reliable method of identifying and monitoring parameters associated with heart failure and pulmonary hypertension with minimal user training.

As one example, inputting the SCG data, the PCG data, and/or the ECG data into the machine learning model for pulmonary artery pressure and cardiac synchrony comprises inputting the SCG data and the PCG data into the machine learning model as a combined oscillation signal, as optionally indicated at 312. As another example, inputting the SCG data, the PCG data, and/or the ECG data into the machine learning model for pulmonary artery pressure and cardiac synchrony comprises inputting the SCG data and the PCG data into the machine learning model as independent data streams, as optionally indicated at 314. As such, the combined oscillation signal and the electrical signal may be to the machine learning model as two inputs. Alternatively, each of the sensors (e.g., the accelerometer, the microphone, and the electrical sensor) may provide an independent data stream to the machine learning model so that the three axes of acceleration, the audio data, and the ECG data form independent inputs.

It may be understood that in some examples, the machine learning model may use only the oscillation data (e.g., the SCG data and/or the PCG data) or only the electrical data as an input. For example, data may be omitted when it is unavailable or of poor quality. As an illustrative example, the ECG data may be unavailable when the digital stethoscope is not in direct contact with the subject's skin, such as when the digital stethoscope is used over clothes. However, inputting both the oscillation data and the electrical data may increase an accuracy of the pulmonary artery pressure and cardiac synchrony output by the machine learning model. Further, the machine learning model may analyze each data stream independently or combine the information from the oscillation data and the electrical data.

At 316, the method 300 optionally includes inputting locations of the accelerometer, the microphone, and the ECG electrodes into the machine learning model. Accelerometers, microphones, and ECG electrodes placed at different locations on the chest wall provide different views of the mechanical and electrical activation of the heart. Thus, the relative positioning of these sensors with respect to the heart may also be input into the machine learning model. For example, a murmur found at the upper left sternal border provides different information from a murmur found at the apex of the heart.

The accelerometer and microphone may also provide inputs on lung sounds and any abnormalities detected therein. The lung sounds may be identified and separated from the heart sounds by the machine learning model. For example, a frequency content of the SCG data and the PCG data may be evaluated to identify lung sounds versus heart sounds. Moreover, knowledge of the locations of the sensors may provide information on whether the sensor is expected to pick up predominantly heart sounds or lung sounds. Abnormalities in lung sounds may be indicative of fluid accumulation that may cause changes to the pulmonary artery pressure and cardiac synchronization. Further, the machine learning model may distinguish lung oscillations from heart oscillations in the PCG data and SCG data, such as by identifying particular audio characteristics in the lung oscillations indicative of wheeze, crackles, rhonchi, cough, or other lung sounds that may be associated with pulmonary ailments.

In some examples, the location of the digital stethoscope with respect to the heart may be input by the user (e.g., via the user interface). Further, an orientation of the digital stethoscope may be determined based on measurements from the accelerometer. In particular, the orientation may be computed while the digital stethoscope is not moving. For example, the one or more processors may determine an angle of the digital stethoscope in each of the three axes of the accelerometer with respect to a three-dimensional world coordinate frame based on acceleration due to gravity measured in each of the three axes, and this angle may specify the orientation. The information input by the user may be used in addition to the determined orientation to approximate the location of each sensor with respect to the heart.

Further, inputting the locations of the accelerometer, the microphone, and the ECG electrodes may additionally include inputting the relative positioning of each sensor with respect to each other in addition to the anatomical location of the sensors on the subject with respect to the heart. For example, the accelerometer may be placed a fixed distance from the microphone (e.g., fixed by the geometry of the digital stethoscope), and as such, the accelerometer may capture oscillations the fixed distance from the microphone, which may result in the microphone and the accelerometer differently capturing the same mechanical activity of the heart.

At 318, the method 300 includes estimating the pulmonary artery pressure and/or the cardiac synchrony via the machine learning model based on the received inputs. For example, the machine learning model may be trained using inputs from the digital stethoscope along with the corresponding invasively measured pulmonary artery pressure and echocardiographic imaging results. The machine learning model may estimate one or both of the pulmonary artery pressure and the cardiac synchrony. For example, the machine learning model may use a first model to determine the pulmonary artery pressure and a second model to determine the cardiac synchrony. Further, in some examples, the machine learning model may estimate or detect additional features that may be indicative of cardiac pathologies, such as ejection fraction, presence of an S3 heart sound, presence of a murmur, etc., or lung pathologies, such as wheeze, crackles, rhonchi, cough, etc.

At 320, the method 300 includes determining a heart failure status and/or a pulmonary hypertension status of the subject based on the estimated pulmonary artery pressure and/or the estimated cardiac synchrony via a decision logic. For example, the decision logic may receive the estimated pulmonary artery pressure and the cardiac synchrony (as well as any other detected features, such as murmurs, identified lung sounds, etc.) output by the machine learning model, which are both analog metrics having a magnitude. The decision logic may use fuzzy logic or a rules-based approach, for example, to determine the heart failure status and the pulmonary hypertension status of the subject based on the magnitude of each metric according to clinical guidelines, as will be elaborated below.

The method 300 optionally includes inputting signals from additional sensors monitoring the subject and/or medical or demographic information of the subject into the decision logic, as indicated at 322. For example, the medical information may include a medical history of the subject, including vital signs, a family disease history, a medication history, and any current or previous symptoms and medical conditions. The demographic information may include age, race, ethnicity, gender, etc. For example, heart disease may be more prevalent in some demographics relative to others, and so the decision logic may utilize the additional information to increase a diagnostic accuracy of the output. The medical history and/or the demographic information may be input into the computing device (e.g., via the user interface of the computing device) and/or accessed via an electronic medical record.

The heart failure status may include one or more of a presence or absence of heart failure, a heart failure risk score or risk classification, a heart failure severity score or severity classification, and a heart failure subtype. Similarly, the pulmonary hypertension status may include one or more of a presence or absence of pulmonary hypertension, a pulmonary hypertension risk score or risk classification, a pulmonary hypertension severity score or severity classification, and a pulmonary hypertension subtype. When the method 300 is used for monitoring changes in an underlying cardiac pathology, the decision logic may infer changes in the underlying condition based on changes to the heart failure status and/or the pulmonary hypertension status.

As one example, the decision logic may utilize a heart failure scoring function that weighs parameters that increase a likelihood of heart failure against parameters that decrease a likelihood of heart failure to determine an overall heart failure score. Further, when the decision logic identifies an absence of heart failure, the heart failure score may classify the subject as having a low risk of developing heart failure, a moderate risk of developing heart failure, and a high risk of developing heart failure. Similarly, when heart failure is detected, the decision logic may identify a subtype, class, and/or severity of the heart failure. Subtypes of heart failure may include heart failure with reduced ejection fraction (HFrEF), heart failure with preserved ejection fraction (HFpEF), left-sided heart failure, right-sided heart failure, systolic dysfunction, diastolic dysfunction, New York Heart Association (NYHA) Class I heart failure, NYHA Class II heart failure, NYHA Class III heart failure, NYHA Class IV heart failure, Stage A heart failure, Stage B heart failure, Stage C heart failure, Stage D heart failure, compensated heart failure, and decompensated heart failure.

As another example, the decision logic may indicate a presence or absence of pulmonary hypertension by comparing the estimated pulmonary artery pressure output by the machine learning model to a pulmonary hypertension threshold. The pulmonary hypertension threshold may be approximately 20 mmHg, for example, above which pulmonary hypertension is indicated. Further, the decision logic may classify a subtype and/or severity of the pulmonary hypertension. For example, the severity classifications may include no pulmonary hypertension, mild pulmonary hypertension, moderate pulmonary hypertension, and severe pulmonary hypertension, each corresponding to a different range of pulmonary artery pressures. The subtypes of pulmonary hypertension may include pulmonary arterial hypertension (PAH), pulmonary hypertension due to left heart disease, pulmonary hypertension due to lung diseases and/or hypoxia, chronic thromboembolic pulmonary hypertension (CTEPH), and pulmonary hypertension with unclear multifactorial mechanisms.

In some embodiments, the decision logic may also determine a condition of the lungs of the subject based on the identified lung sounds. For example, the decision logic may include pre-programmed criteria for scoring pulmonary ailments. As an illustrative example, wheezing may be associated with allergies, bronchitis, emphysema, chronic obstructive pulmonary disease (COPD), pneumonia, and other conditions, while crackles may be caused by pneumonia, heart disease, bronchitis, COPD and other conditions. The decision logic may use the identified lung sounds as well as any additional medical history and demographic information to distinguish between conditions and diseases having similar symptoms. The determined condition of the lungs may include one or more suspected or potential pulmonary ailments when the decision logic is unable to distinguish a single potential underlying condition.

At 324, the method 300 includes outputting the pulmonary artery pressure, the cardiac synchrony, the heart failure status, and/or the pulmonary hypertension status of the subject. The pulmonary artery pressure, the cardiac synchrony, the heart failure status, and/or the pulmonary hypertension status of the subject may be output to the user interface of the computing device, for example. Additionally or alternatively, the pulmonary artery pressure, the cardiac synchrony, the heart failure status, and/or the pulmonary hypertension status of the subject may be output to the electronic medical record of the subject. Any or all of a presence or absence of each condition (e.g., heart failure and pulmonary hypertension), a risk score of the condition, a severity of the condition, and a subtype of the condition may be output, as discussed above and further illustrated in FIG. 4. When the method 300 is used for monitoring a known condition or risk, the method 300 may additionally include outputting a change in the condition or risk level. Further, when lung sounds are evaluated, the method 300 also includes outputting the condition of the lungs of the subject.

At 326, the method 300 optionally includes determining a recommended follow-up action based on the pulmonary artery pressure, the cardiac synchrony, the heart failure status, and/or the pulmonary hypertension status of the subject. For example, the decision logic may determine a recommended exam or procedure to confirm the diagnosis of pulmonary hypertension or heart failure, such as imaging procedures or other diagnostic tests. As another example, the decision logic may output recommendations for treatments or life style changes for the subject to discuss with the clinician. The recommended follow-up action may be dependent on the severity or type of pulmonary hypertension or heart failure detected, for example. As an illustrative example, the recommended follow-up action may include guidelines for a low salt diet both when pulmonary hypertension is present and when the subject has a moderate to high risk of pulmonary hypertension. As another example, the recommended follow-up action may include potential adjustments to treatment based on the determined change in the condition or risk level when the method 300 is used for monitoring the subject over time.

At 328, the method 300 optionally includes outputting the recommended follow-up action. For example, the recommended follow-up action may be output via the user interface of the computing device, such as via a visual message. As another example, the recommended follow-up action may be output to the electronic medical record of the subject, which may be accessible by the clinician and/or the subject (e.g., via a patient portal). As still another example, the recommended follow-up action may be sent to the clinician and/or the subject via a secure message. The method 300 may then end.

In this way, heart failure and pulmonary hypertension may be detected and/or tracked over time. For example, the clinician may use the digital stethoscope while evaluating the subject and use the pulmonary artery pressure, the cardiac synchrony, the pulmonary hypertension status, and/or the heart failure status output by the method along with other information gathered from the evaluation to decide on a treatment plan or whether to refer the patient for further diagnostic testing. As another example, the subject may already be diagnosed with (or at known risk of) heart failure/pulmonary hypertension and use the digital stethoscope to record their own PCG data, SCG data, and ECG data and obtain an output indicating a change in their pulmonary artery pressure, cardiac synchronization, and/or heart failure/pulmonary hypertension status. Further, in some embodiments, the results may be automatically communicated to the clinician so that the clinician may decide if further evaluation of the subject is desired.

Figure 4:
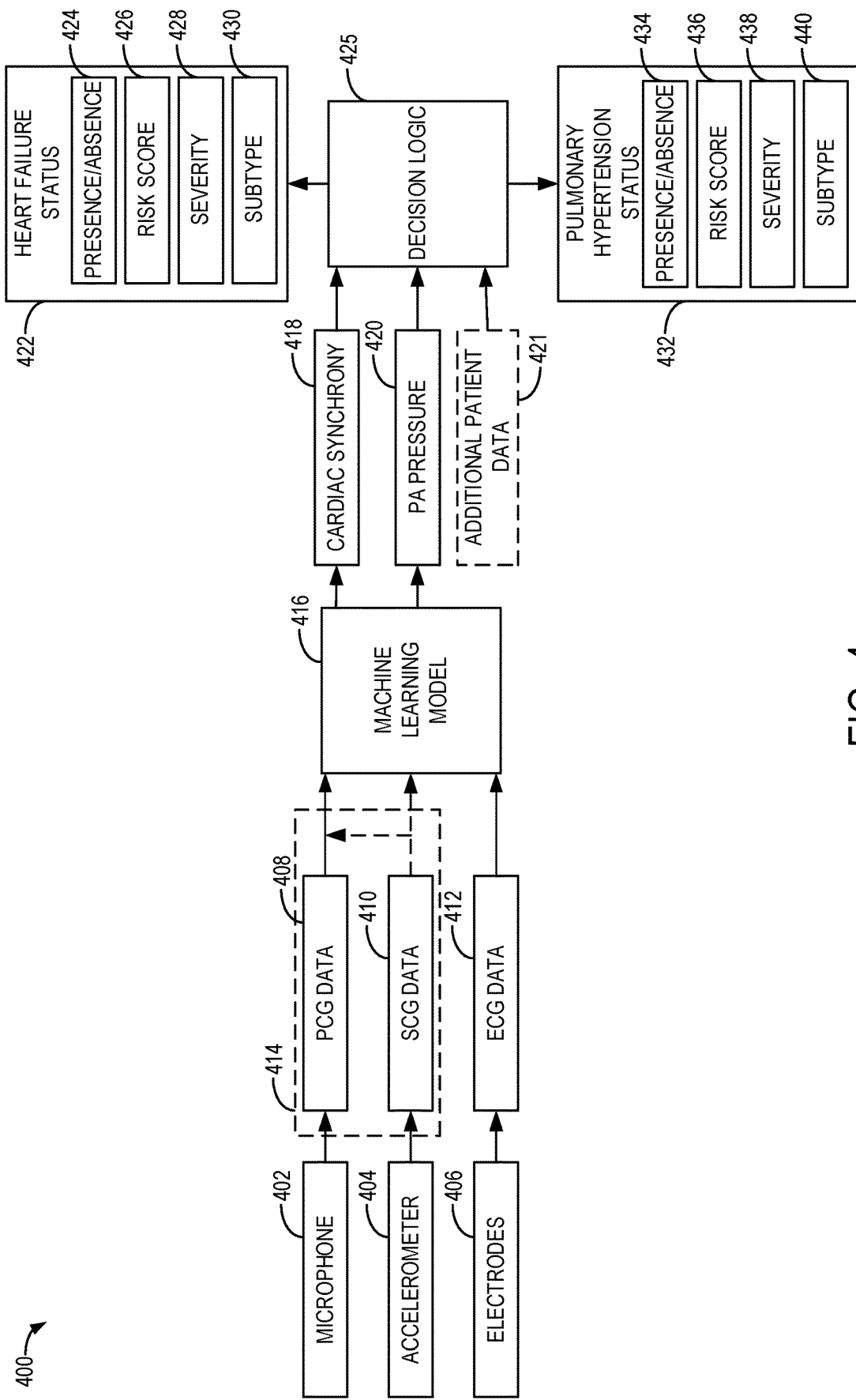
FIG. 4 schematically shows a block diagram of a machine learning-based algorithm for determining and monitoring heart failure and pulmonary hypertension.

Next, FIG. 4 schematically shows an algorithm 400 for identifying and monitoring heart failure and pulmonary hypertension of a patient, such as according to the method 300 of FIG. 3. For example, the algorithm 400 may be executed by a computing device that is in electronic communication with a digital stethoscope, such as the external computing device 202 and the electronic stethoscope 200 of FIG. 2. A microphone 402, an accelerometer 404, and electrodes 406 of the digital stethoscope acquire time-synchronized data from the patient. In particular, the microphone 402 acquires PCG data 408, the accelerometer 404 acquires SCG data 410, and the electrodes 406 acquire ECG data 412. These data are input into a machine learning model 416. In some embodiments, the PCG data 408 and the SCG data 410 are combined into a single oscillation data stream 414 before being input into the machine learning model 416. In other embodiments, the PCG data 408 and the SCG data 410 are fed to the machine learning model 416 as separate inputs.

The machine learning model 416 processes the input data and outputs a cardiac synchrony 418 and a pulmonary artery (PA) pressure 420. The cardiac synchrony 418 and the PA pressure 420 are further input into a decision logic 425. The decision logic 425 may use fuzzy logic or rules-based logic that is programmed according to clinically-relevant cardiac synchrony and pulmonary artery pressure values for different heart failure states and pulmonary hypertension states. In some embodiments, the decision logic 425 may receive additional patient data 421. The additional patient data 421 may comprise any or all of patient demographic information, a medical history of the patient, and outputs from additional sensors and monitors that may be separate from the sensors of the digital stethoscope. For example, the decision logic 425 may receive additional patient data from one or more of a weight scale, an activity monitor, a blood pressure monitor, a pulse oximeter, and a respiration monitor.

The decision logic 425 outputs a heart failure status 422 and a pulmonary hypertension status 432 of the patient. The heart failure status 422 may include any or all of a presence/absence indicator 424, a risk score 426, a severity 428, and a subtype 430 of heart failure. Similarly, the pulmonary hypertension status 432 may include any or all of a presence/absence indicator 434, a risk score 436, a severity 438, and a subtype 440 of heart failure. These outputs may be communicated to the patient and/or a treating physician, such as elaborated above with respect to FIG. 3.

In this way, an approach is provided for non-invasively determining cardiac synchrony and a pulmonary artery pressure of a subject based on signals acquired via a digital stethoscope. The pulmonary artery pressure and the cardiac synchrony may be further used to determine a heart failure status and a pulmonary hypertension status of the subject. As a result, heart failure and pulmonary hypertension may be more inexpensively, quickly, and reliably detected and monitored. Further, patient discomfort during the detection and monitoring may be decreased due to the rapid and non-invasive cardiac synchrony and pulmonary artery pressure estimation. Through the early identification and monitoring of individuals having and at risk of pulmonary hypertension and heart failure, patient outcomes may be increased with decreased provider burden and decreased costs.

The technical effect of estimating cardiac synchrony and pulmonary artery pressure via a machine learning model based on PCG data, SCG data, and/or ECG data received from a digital stethoscope is that an amount of time and an expense of diagnosing heart failure and pulmonary hypertension may be decreased while an accuracy of the diagnosis and patient comfort during the diagnosis is increased.

The disclosure also provides support for a method, comprising: acquiring at least one of electrocardiogram (ECG) data, phonocardiogram (PCG) data, and seismocardiogram (SCG) data from a subject via a digital stethoscope, inputting one or more of the ECG data, the PCG data, and the SCG data into a machine learning algorithm, and estimating at least one of a pulmonary artery pressure and a cardiac synchronization of the subject using the machine learning algorithm. In a first example of the method, the PCG data comprises higher frequency oscillations produced by a heart of the subject and captured by a microphone of the digital stethoscope, and the SCG data comprises lower frequency oscillations produced by the heart of the subject and captured by an accelerometer of the digital stethoscope. In a second example of the method, optionally including the first example, the accelerometer is a three-axis accelerometer configured to capture both transverse and longitudinal oscillations produced by the heart of the subject. In a third example of the method, optionally including one or both of the first and second examples, a relative positioning of each of the microphone and the accelerometer with respect to each other and with respect to the heart is input into the machine learning algorithm. In a fourth example of the method, optionally including one or more or each of the first through third examples, the method further comprises: distinguishing lung oscillations from heart oscillations via the machine learning algorithm based on one or more of a frequency content of the PCG data and the SCG data and the relative positioning of each of the microphone and the accelerometer with respect to each other and with respect to the heart, and outputting a condition of lungs of the subject based on the distinguished lung oscillations. In a fifth example of the method, optionally including one or more or each of the first through fourth examples, the machine learning algorithm receives the PCG data from the microphone and the SCG data from the accelerometer as separate inputs. In a sixth example of the method, optionally including one or more or each of the first through fifth examples, the higher frequency oscillations produced by the heart of the subject and captured by the microphone of the digital stethoscope and the lower frequency oscillations produced by the heart of the subject and captured by the accelerometer of the digital stethoscope are combined into a single oscillation data stream for input into the machine learning algorithm. In a seventh example of the method, optionally including one or more or each of the first through sixth examples, the ECG data comprises 1 to 12 different vectors of electrical polarization of a heart of the subject captured by 1 to 12 ECG leads. In an eighth example of the method, optionally including one or more or each of the first through seventh examples, the ECG data, the PCG data, and the SCG data are time-synchronized. In a ninth example of the method, optionally including one or more or each of the first through eighth examples, the method further comprises: outputting a heart failure subtype, a heart failure severity, or a heart failure risk score of the subject based on at least one of the pulmonary artery pressure and the cardiac synchronization of the subject estimated by the machine learning algorithm. In a tenth example of the method, optionally including one or more or each of the first through ninth examples, the method further comprises: outputting a pulmonary hypertension subtype, a pulmonary hypertension severity, or a pulmonary hypertension risk score of the subject based on at least one of the pulmonary artery pressure and the cardiac synchronization of the subject estimated by the machine learning algorithm. In an eleventh example of the method, optionally including one or more or each of the first through tenth examples, the method further comprises: tracking changes in at least one of the estimated pulmonary artery pressure and the estimated cardiac synchronization of the subject over time, and inferring changes in an underlying condition of the subject over the time based on the tracked changes in at least one of the estimated pulmonary artery pressure and the estimated cardiac synchronization of the subject.

The disclosure also provides support for a method, comprising: acquiring electrocardiogram (ECG) data, phonocardiogram (PCG) data, and seismocardiogram (SCG) data from a subject via a digital stethoscope, inputting at least one of the ECG data, the PCG data, and the SCG data into a machine learning algorithm, inputting signals from at least one of a weight scale, a blood pressure monitor, a respiration monitor, and a pulse oximeter into the machine learning algorithm, and outputting at least one of an estimated pulmonary artery pressure and an estimated cardiac synchrony of the subject from the machine learning algorithm, and outputting a condition of the subject determined based on at least one of the estimated pulmonary artery pressure and the estimated cardiac synchrony. In a first example of the method, the condition of the subject comprises at least one of a presence or absence of heart failure, a risk score of the heart failure, a subtype of the heart failure, and a severity of the heart failure. In a second example of the method, optionally including the first example, the condition of the subject comprises at least one of a presence or absence of pulmonary hypertension, a risk score of the pulmonary hypertension, a subtype of the pulmonary hypertension, and a severity of the pulmonary hypertension.

The disclosure also provides support for a system for performing a cardiac exam, comprising: a digital stethoscope, and a processor operatively coupled to a memory storing instructions that, when executed by the processor, cause the processor to: capture longitudinal chest oscillations, transverse chest oscillations, and electrical signals of a heart via the digital stethoscope, input the longitudinal chest oscillations, the transverse chest oscillations, and the electrical signals of the heart into a machine learning model, and determine a presence or absence of a cardiac pathology based on outputs of the machine learning model. In a first example of the system, the digital stethoscope comprises a microphone, an electrocardiogram (ECG) sensor, and an accelerometer. In a second example of the system, optionally including the first example, the longitudinal chest oscillations are captured by at least one of the microphone and the accelerometer, the transverse chest oscillations are captured by the accelerometer, and the electrical signals are captured by the ECG sensor. In a third example of the system, optionally including one or both of the first and second examples, the cardiac pathology comprises at least one of pulmonary hypertension, heart disease, heart failure, systolic dysfunction, and diastolic dysfunction and further includes a stage or class of the cardiac pathology. In a fourth example of the system, optionally including one or more or each of the first through third examples, the system further comprises: a user interface, and wherein the memory includes further instructions that, when executed by the processor, cause the processor to: output the presence or absence of the cardiac pathology to the user interface, determine a recommended follow-up action based on the presence of the cardiac pathology, and output the recommended follow-up action to the user interface.

As used herein, an element or step recited in the singular and preceded with the word "a" or "an" should be understood as not excluding plural of said elements or steps, unless such exclusion is explicitly stated. Furthermore, references to "one embodiment" of the present invention are not intended to be interpreted as excluding the existence of additional embodiments that also incorporate the recited features. Moreover, unless explicitly stated to the contrary, embodiments "comprising," "including," or "having" an element or a plurality of elements having a particular property may include additional such elements not having that property. The terms "including" and "in which" are used as the plain-language equivalents of the respective terms "comprising" and "wherein." Moreover, the terms "first," "second," and "third," etc. are used merely as labels, and are not intended to impose numerical requirements or a particular positional order on their objects.

This written description uses examples to disclose the invention, including the best mode, and also to enable a person of ordinary skill in the relevant art to practice the invention, including making and using any devices or systems and performing any incorporated methods. The patentable scope of the invention is defined by the claims, and may include other examples that occur to those of ordinary skill in the art. Such other examples are intended to be within the scope of the claims if they have structural elements that do not differ from the literal language of the claims, or if they include equivalent structural elements with insubstantial differences from the literal languages of the claims.

The invention claimed is:

1. A method executable via a processor by executing instructions stored in memory, comprising:
   training a machine learning model to output at least one of an estimated pulmonary artery pressure and an estimated cardiac synchrony, wherein training the machine learning model comprises inputting electrocardiogram (ECG) data, phonocardiogram (PCG) data, and seismocardiogram (SCG) data acquired by a handheld digital stethoscope and corresponding invasively measured pulmonary artery pressure and echocardiographic imaging results;
   acquiring the ECG data, the PCG data, and the SCG data from a subject via a microphone, an electrocardiogram (ECG) sensor, and an accelerometer of the handheld digital stethoscope in order to capture electrical signals, longitudinal chest oscillations, and transverse chest oscillations of a heart of the subject, each of the microphone, the ECG sensor, and the accelerometer coupled to and/or included within a housing of the handheld digital stethoscope;
combining the PCG data and the SCG data into a single oscillation data stream;
inputting the ECG data, the PCG data, the SCG data, and locations of the accelerometer, the microphone, and the ECG sensor with respect to the heart of the subject into the trained machine learning algorithm, wherein the ECG data, the PCG data, and the SCG data is time-synchronized;
inputting signals from at least one of a weight scale, a blood pressure monitor, a respiration monitor, and a pulse oximeter into the machine learning algorithm; and
outputting at least one of the estimated pulmonary artery pressure and the estimated cardiac synchrony of the subject from the machine learning algorithm; and
outputting a condition of the subject determined based on at least one of the estimated pulmonary artery pressure and the estimated cardiac synchrony, the condition including a presence or absence of a cardiac pathology;
wherein the ECG sensor and the microphone are positioned on a first flat surface on an exterior of the housing, wherein the accelerometer is a three-axis accelerometer rigidly affixed to an internal surface of the handheld digital stethoscope, and wherein a second flat surface on the exterior of the housing, opposite to the first flat surface and parallel to the first flat surface, comprises a user control configured to receive input from a user.

2. The method of claim 1, wherein the cardiac pathology comprises heart failure, and wherein the condition further includes at least one of a risk score of the heart failure, a subtype of the heart failure, and a severity of the heart failure.

3. The method of claim 1, wherein the cardiac pathology comprises pulmonary hypertension, and wherein the condition further includes at least one of a risk score of the pulmonary hypertension, a subtype of the pulmonary hypertension, and a severity of the pulmonary hypertension.

4. A system for performing a cardiac exam, comprising:
a handheld digital stethoscope comprising a microphone, an electrocardiogram (ECG) sensor, and an accelerometer each coupled to and/or included within a housing; and
a processor operatively coupled to a memory storing instructions that, when executed by the processor, cause the processor to:
capture longitudinal chest oscillations, transverse chest oscillations, and electrical signals of a heart via the digital stethoscope, wherein capturing longitudinal chest oscillations, transverse chest oscillations, and electrical signals of the heart via the digital stethoscope comprises capturing higher frequency chest oscillations as phonocardiogram (PCG) data with the microphone of the digital stethoscope, lower frequency chest oscillations as seismocardiogram (SCG) data with the accelerometer of the digital stethoscope, and the electrical signals of the heart as ECG data with the ECG sensor of the digital stethoscope, wherein the PCG data, the SCG data, and the ECG data are time-synchronized;
input the longitudinal chest oscillations, the transverse chest oscillations, the electrical signals of the heart, and locations of the accelerometer, the microphone, and the ECG sensor directly into a machine learning model trained to output an estimated pulmonary artery pressure and an estimated cardiac synchrony based on the longitudinal chest oscillations, the transverse chest oscillations, and the electrical signals of the heart and the locations of the accelerometer, the microphone, and the ECG sensor, wherein the locations of the accelerometer, the microphone, and the ECG sensor with respect to the heart are determined based on a location of the digital stethoscope indicated via user input to a user interface and an orientation of the digital stethoscope determined from the SCG data;
output the estimated pulmonary artery pressure and the estimated cardiac synchrony to a user interface;
enter the estimated pulmonary artery pressure and the estimated cardiac synchrony as inputs to a decision logic, wherein the decision logic uses fuzzy logic or rules-based logic that is programmed according to clinically-relevant cardiac synchrony and pulmonary artery pressure values for different heart failure states and pulmonary hypertension states;
receive a heart failure status and a pulmonary hypertension status of the heart as outputs by the decision logic;
determine the presence or absence of a cardiac pathology based on the heart failure status and the pulmonary hypertension status, wherein the cardiac pathology comprises at least one of pulmonary hypertension, heart disease, heart failure, systolic dysfunction, and diastolic dysfunction; and
output the presence or absence of the cardiac pathology to the user interface;
wherein the machine learning model is trained using longitudinal chest oscillations, transverse chest oscillations, and electrical signals of one or more hearts as inputs along with corresponding invasively measured pulmonary artery pressure and echocardiographic imaging results; and
wherein the ECG sensor and the microphone are positioned on a first flat exterior surface of the housing, wherein the accelerometer is a three-axis accelerometer rigidly affixed to an internal surface of the digital stethoscope, and wherein a second flat exterior surface of the housing, opposite to the first flat exterior surface and parallel to the first flat exterior surface, comprises a user control configured to receive input from a user.

5. The system of claim 4, wherein the cardiac pathology comprises at least one of pulmonary hypertension, heart disease, heart failure, systolic dysfunction, and diastolic dysfunction and further includes a stage or class of the cardiac pathology.

6. The system of claim 5, wherein the memory includes further instructions that, when executed by the processor, cause the processor to:
output the presence or absence of the cardiac pathology to the user interface;
determine a recommended follow-up action based on the presence of the cardiac pathology; and
output the recommended follow-up action to the user interface.

7. The system of claim 5, wherein the memory includes further instructions that, when executed by the processor, cause the processor to determine a heart failure status and/or a pulmonary hypertension status based on the estimated pulmonary artery pressure and/or the estimated cardiac synchrony output by the machine learning model via the decision logic.

8. The system of claim 7, wherein the heart failure status comprises one or more of a presence or absence of heart failure, a heart failure risk score or risk classification, a heart failure severity score or severity classification, and a heart failure subtype, and wherein the pulmonary hypertension status comprises one or more of a presence or absence of pulmonary hypertension, a pulmonary hypertension risk score or risk classification, a pulmonary hypertension severity score or severity classification, and a pulmonary hypertension subtype.

9. The system of claim 8, wherein the memory includes further instructions that, when executed by the processor, cause the processor to input signals from at least one of a weight scale, a blood pressure monitor, a respiration monitor, and a pulse oximeter into the decision logic.

10. The system of claim 4, wherein the lower frequency chest oscillations include longitudinal and transverse chest oscillations occurring at a frequency of less than 50 Hz, and wherein the higher frequency chest oscillations include longitudinal chest oscillations occurring at a frequency of greater than 20 Hz.

11. The system of claim 4, wherein inputting the locations of the accelerometer, the microphone, and the ECG sensor directly into the machine learning model comprises inputting a relative positioning of each of the microphone, the ECG sensor, and the accelerometer with respect to each other and inputting an anatomical location of each of the microphone, the ECG sensor, and the accelerometer on a subject with respect to the heart.

12. The system of claim 4, wherein the ECG sensor is configured to measure intrathoracic impedance, and wherein the intrathoracic impedance measured by the ECG sensor is input into the machine learning model, and wherein the machine learning model uses the intrathoracic impedance and the microphone to output a measure of pulmonary fluid retention.

13. The system of claim 4, wherein the digital stethoscope further comprises a first button configured to control an intensity of an amplified audio signal transmitted from the digital stethoscope to an earpiece of a user and a second button configured to stop and/or start measurement of data by the microphone, the ECG sensor, and the accelerometer.

14. The system of claim 4, wherein the decision logic utilizes a heart failure scoring function that weighs parameters that increases a likelihood of heart failure against parameters that decrease the likelihood of heart failure to determine an overall heart failure score.

15. The system of claim 4, wherein the digital stethoscope comprises a second user control on a side of the housing connecting the first flat exterior surface to the second flat exterior surface.

* * * * *